(12) United States Patent
Pevarello et al.

(10) Patent No.: US 6,218,418 B1
(45) Date of Patent: Apr. 17, 2001

(54) 3(5)-AMINO-PYRAZOLE DERIVATIVES, PROCESS FOR THEIR PREPARATION AND THEIR USE AS ANTITUMOR AGENTS

(75) Inventors: Paolo Pevarello, Pavia; Paolo Orsini, Varese; Gabriella Traquandi; Mario Varasi, both of Milan, all of (IT); Edward L. Fritzen; Martha A. Warpehoski, both of Portage, MI (US); Betsy S. Pierce, Kalamazoo, MI (US); Maria Gabriella Brasca, Cusago (IT)

(73) Assignees: Pharmacia & Upjohn S.p.A, Milan (IT); Pharmacia & Upjohn Co., Kalamazoo, MI (US)

( * ) Notice: Subject to any disclaimer, the term of this patent is extended or adjusted under 35 U.S.C. 154(b) by 0 days.

(21) Appl. No.: 09/667,603

(22) Filed: Sep. 22, 2000

Related U.S. Application Data

(63) Continuation of application No. 09/560,400, filed on Apr. 28, 2000, which is a continuation of application No. 09/372,831, filed on Aug. 12, 1999.

(51) Int. Cl.[7] .................. A61K 31/415; A61P 35/00; C07D 231/40
(52) U.S. Cl. .................. 514/404; 544/355; 546/275.4; 548/248; 548/364.4; 548/364.7; 548/365.7; 548/372.1; 548/372.5
(58) Field of Search ................ 548/372.5, 372.1; 514/404

(56) References Cited

U.S. PATENT DOCUMENTS 5,916,908  6/1999  Giese et al. .

FOREIGN PATENT DOCUMENTS

| WO 96/14843 | 5/1996 | (WO) . |
| WO 98/24768 | 6/1998 | (WO) . |
| WO 98/52941 | 11/1998 | (WO) . |
| WO 99/32111 | 7/1999 | (WO) . |

OTHER PUBLICATIONS

Tomoko Hosoi et al., "Evidence for CDK5 as a Major Activity Phosphorylating TAU Protein in Porcine Brain Extract", J. Biochem, vol. 117, pp. 741–749, 1995.
Kevin R. Webster, "The Therapeutic of Targeting the Cell Cycle", Ashley Publications Ltd., Exp. Opin. Invest. Drugs, vol. 7, No. 6, pp. 865–887, 1998.
Chemical Abstracts of Japan, Raymond S. Brinkmeyer et al., "Dimerization of Pyrazolyl–5–Hydroxypyrrolidinones to Tetrazocines", Accession No. 1990:216898, 1990.

*Primary Examiner*—Robert W. Ramsuer
(74) *Attorney, Agent, or Firm*—Oblon, Spivak, McClelland, Maier & Neustadt, P.C.

(57) ABSTRACT

Compounds which are 3-amino-pyrazole derivatives represented by formula (I):

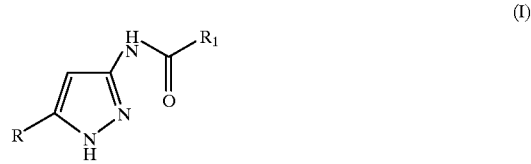

where
R is a $C_3$–$C_6$ cycloalkyl group, which may optionally be substituted by a straight or branched $C_1$–$C_6$ alkyl group, and
$R_1$ is a straight or branched $C_1$–$C_6$ alkyl group or a $C_2$–$C_4$ alkenyl, cycloalkyl, aryl, arylalkyl, arylcarbonyl, aryloxyalkyl and arylalkenyl, which may be optionally substituted; or a pharmaceutically acceptable salt thereof.

The compounds are useful for the treatment of cancer, cell proliferative disorders, Alzheimer's disease, viral infections, auto-immune diseases or neurodegenerative diseases.

25 Claims, No Drawings

3(5)-AMINO-PYRAZOLE DERIVATIVES, PROCESS FOR THEIR PREPARATION AND THEIR USE AS ANTITUMOR AGENTS

This application is a Continuation application of U.S. Ser. No. 09/560,400, filed Apr. 28, 2000, now allowed; which is a Continuation application of U.S. Ser. No. 09/372, 831, filed Aug. 12, 1999, now allowed.

BACKGROUND OF THE INVENTION

1. Field of the Invention

The present invention relates to 3(5)-amino-pyrazole derivatives, to a process for their preparation, to pharmaceutical compositions containing them, and to their use as therapeutic agents, particularly in the treatment of cancer and cell proliferative disorders.

2. Discussion of the Background

Several cytotoxic drugs such as, e.g., fluorouracil (5-FU), doxorubicin and camptothecins, damage DNA or affect cellular metabolic pathways and thus cause, in many cases, an indirect block of the cell cycle. Therefore, by producing an irreversible damage to both normal and tumor cells, these agents result in a significant toxicity and side-effects.

In this respect, compounds capable of functioning as highly specific antitumor agents by selectively leading to tumor cell arrest and apoptosis, with comparable efficacy but reduced toxicity than the currently available drugs, are desirable.

It is well known that progression through the cell cycle is governed by a series of checkpoint controls, otherwise referred to as restriction points, which are regulated by a family of enzymes known as the cyclin-dependent kinases (cdk). In turn, the cdks themselves are regulated at many levels such as, for instance, binding to cyclins.

The coordinated activation and inactivation of different cyclin/cdk complexes is necessary for normal progression through the cell cycle. Both the critical G1-S and G2-M transitions are controlled by the activation of different cyclin/cdk activities. In G1, both cyclin D/cdk4 and cyclin E/cdk2 are thought to mediate the onset of S-phase. Progression through S-phase requires the activity of cyclin. A/cdk2 whereas the activation of cyclin A/cdc2 (cdkl) a cyclin B/cdc2 are required for the onset of metaphases. For a general reference for cyclins and cyclin-dependent kinases see, for instance, Kevin R. Webster et al, in Exp. Opin. Invest. Drugs, 1998, Vol. 7(6), 865–887.

Checkpoint controls are defective in tumor cells due, in part, to disregulation of cdk activity. For example altered expression of cyclin E and cdks has been observed in tumor cells, and deletion of the cdk inhibitor p27 KIP gene in mice has been shown to result in a higher incidence of cancer.

Increasing evidence supports the idea that the cdks are rate-limiting enzymes in cell cycle progression and, as such, represent molecular targets for therapeutic intervention. In particular, the direct inhibition of cdk/cyclin kinase activity should be helpful in restricting the unregulated proliferation of a tumor cell.

SUMMARY OF THE INVENTION

It is an object of the invention to provide compounds which are useful in treating cell proliferative disorders associated with an altered cell dependent kinase activity. It is another object to provide compounds which have cdk/cyclin kinase inhibitory activity.

It is another object of the invention to provide compounds which are useful in therapy as antitumor agents but lack, in terms of both toxicity and side effects, the drawbacks associated with currently available antitumor drugs discussed above.

The present inventors have now discovered that 3-amino-pyrazoles are endowed with cdk/cyclin kinase inhibitory activity and are thus useful in therapy as antitumor agents and lack, in terms of both toxicity and side effects, the aforementioned drawbacks associated with currently available antitumor drugs.

More specifically, the 3-amino-pyrazoles of the invention are useful in the treatment of a variety of cancers including, but not limited to: carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma neuroblastoma, glioma and schwannomas; other tumors, including melanoma, seminoma, teratocarcinoma, osteosarcoma, xenoderoma pigmentosum, keratoctanthoma, thyroid follicular cancer and Kaposi's sarcoma.

Due to the key role of cdks in the regulation of cellular proliferation, the 3-amino-pyrazole derivatives are also useful in the treatment of a variety of cell proliferative disorders such as, for example, benign prostate hyperplasia, familial adenomatosis polyposis, neurofibromatosis, psoriasis, vascular smooth cell proliferation associated with atherosclerosis, pulmonary fibrosis, arthritis glomerulonephritis and post-surgical stenosis and restenosis.

The compounds of the invention may be useful in treatment of Alzheimer's disease, as suggested by the fact that cdk5 is involved in the phosphorylation of tau protein (J. Biochem. 117,741–749,1995).

The compounds of this invention, as modulators of apoptosis, may also be useful in the treatment of cancer, viral infections, prevention of AIDS development in HIV-infected individuals, autoimmune diseases and neurodegenerative disorders.

The compounds of this invention may be useful in inhibiting tumor angiogenesis and metastasis.

The compounds of the invention may also act as inhibitor of other protein kinases, e.g., protein kinase C, her2, raf1, MEK1, MAP kinase, EGF receptor, PDGF receptor, IGF receptor, PI3 kinase, weel kinase, Src, Ab1, and thus be effective in the treatment of diseases associated with other protein kinases.

Accordingly, the present invention provides a method for treating cell proliferative disorders associated with an altered cell dependent kinase activity, by administering to a mammal in need thereof an effective amount of a 3-amino-pyrazole derivative represented by formula (I):

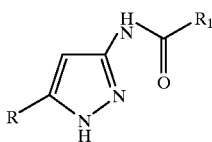

(I)

where
R is a $C_3$–$C_6$ cycloalkyl group optionally substituted by a straight or branched $C_1$—$C_6$ alkyl group;
$R_1$ is a straight or branched $C_1$–$C_6$ allyl, $C_2$–$C_4$ alkenyl, cycloalkyl, aryl, arylalkyl, arylcarbonyl, aryloxyalkyl or arylalkenyl group, which may optionally be substituted by one or more groups selected from the group consisting of cycloalkyl, hydroxy, alkylthio, alkoxy, amino, alkylamino, dialkylamino, alkoxycarbonylamino, alkoxycarbonylalkylamino, alkylcarbonyl, alkylsulphonyl, alkoxycarbonyl, carboxy, halogen, nitro, aryloxy, arylthio, arylsulphonyl, N-alkyl-piperazinyl, piperidinyl, 4-morpholinyl, arylamino, cyano, alkyl, aryl, oxo, haloaryl, haloarylalkyl, haloaryloxy, haloarylsulphonyl, aminosulphonyl, aminocarbonyl, arylcarbonyl, perfluorinated alkyl and perfluorinated alkoxy groups;
or a pharmacetically acceptable salt therof.

In a preferred embodiment of the method described above, the cell proliferative disorder is selected from the group consisting of cancer, Alzheimer's disease, viral infections, auto-immune diseases and neurodegenerative disorders.

Specific types of cancer that may be treated include carcinoma, squamous cell carcinoma, hematopoietic tumors of myeloid or lymphoid lineage, tumors of mesenchymal origin, tumors of the central and peripheral nervous system, melanoma, seminoma, teratocarcinoma, osteosarcoma, xenoderoma pigmentosum, keratoctanthoma, thyroid follicular cancer, and Kaposi's sarcoma.

In another preferred embodiment of the method described above, the cell proliferative disorder is selected from the group consisting of benign prostate hyperplasia, familial adenomatosis polyposis, neuro-fibromatosis, psoriasis, vascular smooth cell proliferation associated with atherosclerosis, pulmonary fibrosis, arthritis glomerulonephritis and post-surgical stenosis and restenosis.

In addition, the inventive method provides tumor angiogenesis and metastasis inhibition. The inventive method may also provide cell cycle inhibition or cdk/cyclin dependent inhibition.

The present invention also provides a 3-amino-pyrazole derivative represented by formula (I):

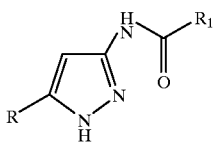

(I)

where
R is a $C_3$–$C_6$ cycloalkyl group optionally substituted by a straight or branched $C_1$–$C_6$ alkyl group;
$R_1$ is a straight or branched $C_1$–$C_6$ alkyl, $C_2$–$C_4$ alkenyl, cycloalkyl, aryl, arylalkyl, arylcarbonyl, aryloxyalkyl or arylalkenyl group, which may be optionally substituted with one or more groups selected from the group consisting of cycloalkyl, hydroxy, alkylthio, alkoxy, amino, alkylamino, dialkylamino, alkoxycarbonylamino, alkoxycarbonylalkylamino, alkylcarbonyl, alkylsulphonyl, alkoxycarbonyl, carboxy, halogen, nitro, aryloxy, arylthio, arylsulphonyl, N-alkyl-piperazinyl, piperidinyl, 4-morpholinyl, arylamino, cyano, alkyl, aryl, oxo, haloaryl, haloarylalkyl, haloaryloxy, haloarylsulphonyl, aminosulphonyl, aminocarbonyl, arylcarbonyl, perfluorinated alkyl and perfluorinated alkoxy groups;
or a pharmacetically acceptable salt therof.

The present invention also includes methods of synthesizing the 3-amino-pyrazole derivative represented by formula (I). A pharmaceutical composition comprising the 3-amino-pyrazole derivative represented by formula (I) is also included in the present invention.

The present invention also includes a compound useful in the synthesis the 3-amino- pyrazole derivative represented by formula (I), which is represented by formula (V):

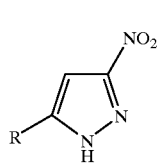

(V)

where R is a $C_3$–$C_6$ cycloalkyl group optionally substituted with a straight or branched $C_1$–$C_6$ alkyl group.

A more complete appreciation of the invention and many of the attendant advantages thereof will be readily obtained as the same becomes better understood by reference to the following detailed description.

DETAILED DESCRIPTION OF THE INVENTION

Several 3-amino-pyrazole derivatives are known as pesticides, herbicides or even as therapeutic agents. Among them are, as an example, heteroaryl-pyrazoles active as p38 kinase inhibitors (WO 98/52941, G. D. Searle and Co.) and other 3-amino-pyrazoles which inhibit protein kinases (WO 96/14843, COR Therapeutics, Inc.).

As will be readily appreciated, the unsubstituted ring nitrogen pyrazoles in the compounds of the invention are known to rapidly equilibrate, in solution, as admixtures of both tautomers:

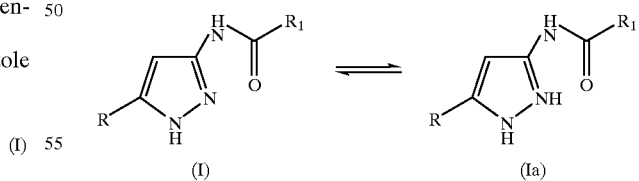

(I)            (Ia)

Accordingly, in the present invention, where only one tautomer is indicated for the compounds of formula (I), the other, (Ia), is also within the scope of the present invention, unless specifically noted otherwise.

As used herein, unless otherwise specified, with the term halogen atom refers to a fluorine, chlorine, bromine or iodine atom.

As used herein, unless otherwise indicated, the terms alkyl and alkoxy include $C_1$–$C_6$ alkyl and $C_1$–$C_6$ alkoxy groups. The terms straight or branched $C_1$–$C_6$ alkyl or $C_1$–$C_6$ alkoxy include methyl, ethyl, n-propyl, isopropyl, n-butyl, isobutyl, sec-butyl, tert-butyl, n-pentyl, n-hexyl, methoxy, ethoxy, n-propoxy, isopropoxy, n-butoxy and the like.

Likewise, the terms alkylthio, alkylamino dialkylamino, alkoxycarbonyl, alkoxycarbonylamino alkylcarbonyl, alkylsulphonyl, alkocarbonyl, N-alkyl-piperazinyl and the like, include groups where the alkyl and alkoxy moieties are $C_1$–$C_6$ aklyl or alkoxy groups.

Unless otherwise specified, with the term cycloalkyl includes a $C_1$–$C_6$ cycloalkyl group such as cyclopropyl, cyclobutyl, cyclopentyl and cyclohexyl as well as cycloalkyl and bridged cycloalkyl groups with, e.g., up to 10 carbon atoms, e.g., an adamantane group.

The term aryl includes mono-, bi- or poly- carbocyclic or heterocyclic hydrocarbons with from 1 to 4 ring moieties, wherein at least one of the rings is aromatic, either fused or linked to each other by single bonds. Thus, these groups may have 5 to 20 carbon atoms. Preferably 6 to 20 carbon atoms.

The term heterocycle, hence encompassing heteroaromatic rings, includes a 5 or membered saturated or unsaturated carbocycle where one or more carbon atoms are replaced by one or more atoms selected from nitrogen, oxygen and sulphur.

Example of preferred aryl groups include phenyl, 1-naphtyl, 2-naphthyl, indanyl, indenyl, biphenyl, benzacycloalkyl, e.g., bicyclo[4.2.0]octa-1,3,5,-triene, benzoheterocyclyl, e.g., benzadioxolyl, quinoxalyl, indolyl, optionally benzocondensed pyrrolyl, furyl, thienyl, imidazolyl pyrazolyl, thiazolyl, oxazolyl, isoxazolyl, pyridyl, pyrazinyl, pyrimidyl and the like.

The term haloaryl, haloarylalkyl, haloarylaxy and haloarylsulphonyl include an aryl, arylalkyl, aryloxy and arylsulphonyl group further substituted by one or more halogen atoms.

The term $C_2$–$C_4$ alkenyl includes a group selected from vinyl, allyl, 1-propenyl, isopropenyl, 1-butenyl, 2-butenyl, 3-butenyl and the like.

The term oxo refers to a carbonyl (>C=O) group.

The term perfluorinated alkyl and alkoxy group includes a $C_1$–$C_4$ alkyl or alkoxy group further substituted by more than one fluorine atom such as, for example, trifluoromethyl, 2,2,2-trifluoroethyl, 1,1,2,2,2-pentafluoroethyl, trifluoromethoxy and the like.

As noted above, $R_1$ may be substituted. The $R_1$ group may be substituted with, for example, one, two or three, or more, of the substituents described above.

Pharmaceutically acceptable salts of the compounds of formula (I) include the acid addition salts with inorganic or organic acids, e.g., nitric, hydrochloric, hydrobromic, sulphuric, perchloric, phosphoric, acetic, trifluoroacetic propionic, glycolic, lactic, oxalic, malonic, malic, maleic, tartaric, citric, benzoic, cinnamic, mandelic, methanesulphonic, isethionic and salicylic acid, as well as the salts with inorganic or organic bases, e.g., alkali or alkaline-earth metals, especially sodium, potassium, calcium or magnesium hydroxides, carbonates or bicarbonates, acyclic or cyclic amines, preferably methylamine, ethylamine, diethylamine, triethylamine or piperidine.

The compounds of formula (I) may have asymmetric carbon atoms and may therefore exist either as racemic admixtures or as individual optical isomers.

Accordingly, the use as an antitumor agent of all possible isomers and their admixtures and of both metabolites and the pharmaceutically acceptable bio-precursors (otherwise referred to as pro-drugs) of the compounds of formula (I) are also within the scope of the present invention.

Preferred compounds of the invention of formula (I) are those where R is a cycloalkyl group and $R_1$ is a $C_1$–$C_4$ allyl, phenyl, phenylalkyl, 5 or 6 membered heteroaryl or heteroarylalkyl group, which may be optionally further substituted as described above.

Even more preferred compounds represented by formula (I) are those where $R_1$ is a $C_1$–$C_4$ alkyl group or a phenyl or phenylalkyl group optionally substituted by hydroxy, halogen, amino, alkoxy, alkoxycarbonyl, phenyl or by a heterocycle such as pyridine, indole, thiophene, thiazole, isoxazole, furan, piperidine and morpholine.

Examples of preferred compounds of the invention, which may be in the form of pharmaceutically acceptable salts, e.g., a hydrobromide or hydrochloride salt, include the following:

N-(5-cyclopropyl-1H-pyrazol-3-yl)-2,2-diphenylacetamide;

N-(3-cyclopropyl-1H-pyrazol-5-yl)-2-(4-nitrophenyl)acetamide;

N-(3-cyclopropyl-1H-pyrazol-5-yl)-4-methoxybenzamide;

N-(3-cyclopropyl-1H-pyrazol-5-yl)-2-(3-methoxyphenyl)acetamide;

N-(3-cyclopropyl-1H-pyrazol-5-yl)-2-[4-(dimethylamino)phenyl]acetamide;

N-(3-cyclopropyl-1H-pyrazol-5-yl)-1-phenylcyclopropancarboxamide;

2-(1,3-benzodioxol-5-yl-N-(3-cyclopropyl-1H-pyrazol-5-yl)acetamide;

N-(3-cyclopropyl-1H-pyrazol-5-yl)-2-(4methoxyphenyl)acetamide;

N-(3-cyclopropyl-1H-pyrazol-5-yl)-2-phenylpropanamide;

N-(3-cyclopropyl-1H-pyrazol-5-yl)-2-(3,4-dimethoxyphenyl)acetamide;

N-(3-cyclopropyl-1H-pyrazol-5-yl)-2-(1H-indol-3-yl)acetamide;

N-(3-cyclopropyl-1H-pyrazol-5-yl)-2-(5-methoxy-1H-indol-3-yl)acetamide;

N-(3-cyclopropyl-1H-pyrazol-5-yl)-2-(1-methyl-1H-indol-3-yl)acetamide;

2-(5-chloro-1-benzothiphen-3-yl)-N-(3-cyclopropyl-1H-pyrazol-5-yl)acetamide;

2-(1-benzothiophen-3-yl)-N-(3-cyclopropyl-1H-pyrazol-5-yl)acetamide;

N-(3-cyclopropyl-1H-pyrazol-5-yl)-3-cyclopentylpropanamide;

2-(4-chlorophenyl)-N-(3-cyclopropyl-1H-pyrazol-5-yl)acetamide;

N-(3-cyclopropyl-1H-pyrazol-5-yl)-4-oxo-4-phenylbutanamide;

N-(3-cyclopropyl-1H-pyrazol-5-yl)-2-(2,3-dihydro-1H-inden-5-yl)acetamide;

3-(2-chlorophenoxyl)-N-(3-cyclopropyl-1H-pyrazol-5-yl)propanamide;

N-(3-cyclopropyl-1H-pyrazol-5-yl)-2-oxo-2-phenylacetamide;

N-(3-cyclopropyl-1H-pyrazol-5-yl)-2-(4-methylphenyl)acetamide;

2-[1,1'-biphenyl]-4-yl-N-(3-cyclopropyl-1H-pyrazol-5-yl)acetamide;
N-(3-cyclopropyl-1H-pyrazol-5-yl)-2-(3-chlorophenyl)acetamide;
N-(3-cyclopropyl-1H-pyrazol-5-yl)-2-(1-naphtyl)acetamide;
N-(3-cyclopropyl-1H-pyrazol-5-yl)-2-(2-fluorophenyl)acetamide;
N-(3-cyclopropyl-1H-pyrazol-5-yl)-2-(2-chlorophenyl)acetamide;
N-(3-cyclopropyl-1H-pyrazol-5-yl)-2-(4-fluorophenyl)acetamide;
N-(3-cyclopropyl-1H-pyrazol-5-yl)-2-(4-trifluoromethyl-phenyl)acetamide;
N-(3-cyclopropyl-1H-pyrazol-5-yl)-2-methoxy-2-phenylacetamide;
N-(3-cyclopropyl-1H-pyrazol-5-yl)-3-oxo-1-indanecarboxamide;
N-(3-cyclopropyl-1H-pyrazol-5-yl)-2-(3-thienyl)acetamide;
N-(3-cyclopropyl-1H-pyrazol-5-yl)bicyclo[4.2.0]octa-1,3,5-triene-7-carboxamide;
N-(3-cyclopropyl-1H-pyrazol-5-yl)-4-phenyl-3-butenamide;
5-[(4-chlorophenyl)sulphonyl]-N-(5-cyclopropyl-1H-pyrazol-3-yl)-3-methyl-2-thiophenecarboxamide;
N-(5-cyclopropyl-1H-pyrazol-3-yl)-4-phenoxybenzamide;
4-bromo-N-(5-cyclopropyl-1H-pyrazol-3-yl)benzamide;
N-(5-cyclopropyl-1H-pyrazol-3-yl)-3,5-bis(trifluoromethyl)benzamide;
N-(5-cyclopropyl-1H-pyrazol-3-yl)-4-bromobenzamide;
N-(5-cyclopropyl-1H-pyrazol-3-yl)-3,3-dimethylbutanamide;
N-(5-cyclopropyl-1H-pyrazol-3-yl)-4-iodobenzamide;
N-(5-cyclopropyl-1H-pyrazol-3-yl)-1-napthamide;
N-(5-cyclopropyl-1H-pyrazol-3-yl)-3-cyanobenzamide;
N-(5-cyclopropyl-1H-pyrazol-3-yl)-1,3-benzodioxole-5-carboxamide;
3-(2-chlorophenyl)-N-(5-cyclopropyl-1H-pyrazol-3-yl)-2-propenamide;
2,5-dichloro-N-(5-cyclopropyl-1H-pyrazol-3-yl)-3-thiophenecarboxamide;
N-(5-cyclopropyl-1H-pyrazol-3-yl)-2-(propylsulfanyl)nicotinamide;
N-(5-cyclopropyl-1H-pyrazol-3-yl)-2,2,5,7-etmethyl-1-oxo-4-indanecarboxamide;
N-(5-cyclopropyl-1H-pyrazol-3-yl)-2-pyridinecarboxamide;
N-(5-cyclopropyl-1H-pyrazol-3-yl)-2-adamantancarboxamide;
N-(5-cyclopropyl-1H-pyrazol-3-yl)-4-methylbenzamide;
N-(5-cyclopropyl-1H-pyrazol-3-yl)-2,3,4,5,6-pentafluorobenzamide;
N-(5-cyclopropyl-1H-pyrazol-3-yl)-2-phenoxyacetamide;
N-(5-cyclopropyl-1H-pyrazol-3-yl)-2-phenylacetamide;
N-(5-cyclopropyl-1H-pyrazol-3-yl)-cyclopentancarboxamide;
N-(5-cyclopropyl-1H-pyrazol-3-yl)-2-(2-thienyl)acetamide;
N-(5-cyclopropyl-1H-pyrazol-3-yl)-3,5-dichlorobenzamide;
2-chloro-N-(5-cyclopropyl-1H-pyrazol-3-yl)-6-methylisonicotinamide;
N-(5-cyclopropyl-1H-pyrazol-3-yl)-5-isoxazolecarboxamide;
2,4-dichloro-N-(5-cyclopropyl-1H-pyrazol-3-yl)-5-fluorobenzamide;
N-(5-cyclopropyl-1H-pyrazol-3-yl)-2,4-difluorobenzamide;
N-(5-cyclopropyl-1H-pyrazol-3-yl)-2,4-chlorobenzamide;
N-(5-cyclopropyl-1H-pyrazol-3-yl)-2-dichlorobenzamide;
N-(5-cyclopropyl-1H-pyrazol-3-yl)-2,6-dichlorobenzamide;
N-(5-cyclopropyl-1H-pyrazol-3-yl)-2-methoxybenzamide;
N-(5-cyclopropyl-1H-pyrazol-3-yl)-2-methlylbenzamide;
N-(5-cyclopropyl-1H-pyrazol-3-yl)-3-fluorobenzamide;
N-(5-cyclopropyl-1H-pyrazol-3-yl)-3-chlorobenzamide;
N-(5-cyclopropyl-1H-pyrazol-3-yl)-3,5-dimethoxybenzamide;
N-(5-cyclopropyl-1H-pyrazol-3-yl)-3-methylbenzamide;
N-(5-cyclopropyl-1H-pyrazol-3-yl)-4-fluorobenzamide;
N-(5-cyclopropyl-1H-pyrazol-3-yl)-4-trifluoromethylbenzamide;
Methyl 4-[(5-cyclopropyl-1H-pyrazol-3-yl)amino]-4-oxobutanoate;
N-(5-cyclopropyl-1H-pyrazol-3-yl)-cyclopropanecarboxamide;
N-(5-cyclopropyl-1H-pyrazol-3-yl)-4-cyanobenzamide;
N-(5-cyclopropyl-1H-pyrazol-3-yl)-2-napthaniide;
N-(5-cyclopropyl-1H-pyrazol-3-yl)-2-thiophenecarboxamide;
N-(5-cyclopropyl-1H-pyrazol-3-yl)-2-quinoxalinecarboxamide;
N-(5-cyclopropyl-1H-pyrazol-3-yl)-3,4-difluorobenzamide;
N-(5-cyclopropyl-1H-pyrazol-3-yl)-3,5-difluorobenzamide;
N-(5-cyclopropyl-1H-pyrazol-3-yl)-3,5-dimethoxybenzamide;
N-(5-cyclopropyl-1H-pyrazol-3-yl)-2-(2,5-dimethoxyphenyl)acetamide;
N-(5-cyclopropyl-1H-pyrazol-3-yl)-2-ethoxybenzamide;
N-(5-cyclopropyl-1H-pyrazol-3-yl)-3,4-dimethoxybenzamide;
N-(5-cyclopropyl-1H-pyrazol-3-yl)-2-phenylbutanamide;
N-(5-cyclopropyl-1H-pyrazol-3-yl)-4-(trifluoromethoxy)benzamide;
3-chloor-N-(5-cyclopropyl-1H-pyrazol-3-yl)-1-benzothiophene-2-carboxamide;
2-(4-chlorophenoxy)-N-(5-cyclopropyl-1H-pyrazol-3-yl)nicotinamide;
3-chloro-N-(5-cyclopropyl-1H-pyrazol-3-yl)-2-thiophenecarboxamide;
N-(3-cyclopropyl-1H-pyrazol-5-yl)acetamide;
N-(3-cyclopropyl-1H-pyrazol-5-yl)benzamide;
4-chloro-N-(3-cyclopropyl-1H-pyrazol-5-yl)benzamide;

N-(3-cyclopropyl-1H-pyrazol-5-yl)-1-benzothiophene-2-carboxamide;

N-(3-cyclopropyl-1H-pyrazol-5-yl)[1,1'-biphenyl]-4-carboxamide;

N-(3-cyclopropyl-1H-pyrazol-5-yl)-3-phenylpropanamide;

Methyl 4-{[(3-cyclopropyl-1H-pyrazo-5-yl)amino]carbonyl}benzoate;

4-{[(3-cyclopropyl-1H-pyrazol-5-yl)amino]carbonyl}benzoic acid;

N-(3-cyclopropyl-1H-pyrazol-5-yl)-3-bromobenzamide;

N-(3-cyclopropyl-1H-pyrazol-5-yl)-3,4dichlorobenzide;

N-(3-cyclopropyl-1H-pyrazol-5-yl)-2-bromobenzamide;

N-(3-cyclopropyl-1H-pyrazol-5-yl)-3-methoxybenzamide;

N-(3-cyclopropyl-1H-pyrazol-5-yl)-3-trifluoromethylbenzamide;

N-(3-cyclopropyl-1H-pyrazol-5-yl)-4-methoxybenzamide;

4-butoxy-N-(3-cyclopropyl-1H-pyrazol-5-yl)benzamide;

N-(3-cyclopropyl-1H-pyrazol-5-yl)-1H-indole-2-carboxamide;

N-(3-cyclopropyl-1H-pyrazol-5-yl)-2-[5-(2,6-difluorobenzyl)-2-methoxyphenyl]acetamide;

$N^1$-(3-cyclopropyl-1H-pyrazol-5-yl)therephthalamide.

The compounds of formula (I), and the salts thereof, may be obtained, for example, by a process comprising:

(a) reacting a compound represented by formula (II):

 (II)

where R is as defined above and $R_2$ is an alkyl group, with acetonitrile in the presence of a basic agent, to obtain a compound represented by formula (III):

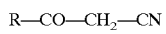 (III)

where R is as defined above;

(b) reacting a compound represented by formula (III) with hydrazine hydrate to obtain a compound represented by formula (IV):

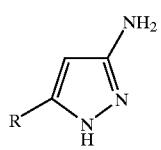 (IV)

where R is as defined above;

(c) oxidizing a compound represented by formula (IV) to obtain a compound represented by formula (V):

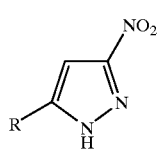 (V)

where R is as defined above;

(d) reacting a compound represented by forrmula (V) with tert-butoxycarbonyl anhydride ($Boc_2O$) to obtain a compound represented by formula (VI):

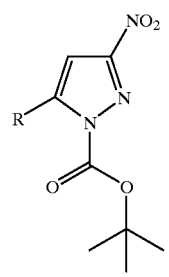 (VI)

where R is as defined above;

(e) reducing a compound represented by formula (VI) to obtain a compound represented by formula (VII):

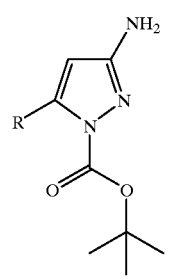 (VII)

where R is as defined above;

(f) reacting a compound represented by formula (VII) with a compound represented by formula (VIII):

 (VIII)

where X is hydroxy and $R_1$ is as defined above, to obtain a compound represented by formula (IX):

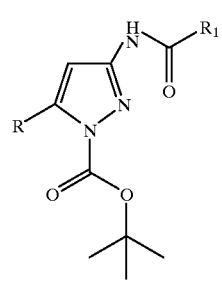 (IX)

where R and $R_1$ are as defined above; and (g) hydrolyzing a compound represented by formula (IX) in an acidic medium to obtain a compound of formula (I), where R and $R_1$ are as defined above; and, if desired, converting a 3-aminopyrazole derivative represented by formula (I) into another derivative represented by formula (I), and/or into a salt thereof.

Alternatively, the compounds represented by formula (I) and pharmaceutically acceptable salts thereof may be obtained by a process comprising:

(a) reacting a compound represented by formula (IV):

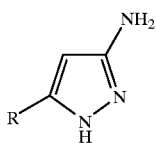

(IV)

with a compound represented by formula (VIII):

$R_1$—COX  (VIII)

where R and $R_1$ are as defined above and X is hydroxy a suitable leaving group, preferably chlorine or bromine, to obtain a compound represented by formula (X):

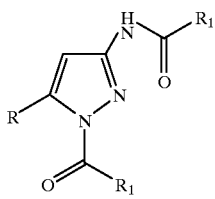

(X)

where R and $R_1$ are as defined above; and (b) selectively hydrolyzing a compound of formula (X) in a basic medium, to obtain a compound represented by formula (I).

As will be readily appreciated, if the compound of formula (I), prepared according to the processes described above, is obtained as an admixture of isomers, its separation into the single isomers of formula (I) according to conventional techniques is within the scope of the present invention.

Likewise, the conversion into the free compound (I) of corresponding salt thereof, according to well-known procedures, is still within the scope of the invention.

The reaction between a compound of formula (IV) and a compound of formula (VIII) wherein X is a suitable leave group can be carried out in the presence of a tertiary base, such as triethylamine, N-methylmorpboline, N,N-diisopropylethylamine or pyridine, in a suitable solve such as toluene, dichloromethane, chloroform, diethylether, tetrahydrofuran, acetonitrile, dioxane or N,N-dimethylformamide, at a temperature ranging from about 10° C. to reflux. The reaction between a compound of formula (IV) and a compound of formula (VIII) can be also carried out the presence of a polymer supported tertiary base such as polystyrene supported N-methylmorpholine in a suitable solvent, for instance toluene, dichloromethane, chlorofom, diethylether, tetrahydrofuran, acetonitrile, dioxane or N,N-dimethylformamide, at room temperature.

The reaction of a compound of formula (X) to produce a compound of formula (I) can be carried out with a base such as sodium hydroxide, potassium hydroxide, sodium carbonate or potassium carbonate in a suitable solvent such as mixture of methanol or ethanol and water at room temperature.

The reaction of a compound of formula (X) to produce compound of formula (I) can be also carried out by using a polystyrene supported trisamine as a basic agent.

The reaction between a compound of formula (VII) and a compound of formula (VIII) where X is a hydroxy group can be carried out in the presence of a coupling agent such as for instance, carbodiimide, i.e., 1,3-dicyclohexylcarbodiimide, 1,3-diisopropylcarbodiimide, or 1-(3-dimethylaminopropyl)-3-ethylcarbodiimide, in a suitable sovlent such as, for example, dichloromethane, chloroform, tetrahydrofuran, diethyl ether, 1,4-dioxane, acetonitrile, toluene, or N,N-dimethylformamide at a temperature ranging from about −10° C. to reflux for a suitable time, i.e., from about 30 min. to about 96 hours.

The reaction between a compound of formula (VII) and compound of formula (VIII) may be also carried out by using a polymer supported coupling agent such as polystyrene supported dicyclohexylcarbodiimide in a suitable solvent such as methylene chloride, chloroform, dioxane, acetonitrile, N,N-dimethylformamide, tetrahydrofuran at room temperature for a time ranging from 12 to 96 hours.

The reaction between a compound of formula (VII) and a compound of formula (VIII) can be also carried out, for example, by a mixed anhydride method, using an alkyl chloroformate such as ethyl, iso-butyl, or iso-propyl chloroformate, in the presence of a tertiary base, such as triethylamine, N,N-diisopropylethylamine or pyridine, in a suitable solvent such as, for instance, toluene, dichloromethane, chloroform, tetrahydrofran, acetonitrile, diethyl ether, 1,4-dioxane, or N,N-dimethylformamide, at a temperature ranging from about −30° C. to room temperature The reaction of a compound of formula (IX) to produce a compound of formula (I) can be carried out with an acid, such as trifluoroacetic acid, hydrochloric acid, formic acid, in a suitable solvent such as methylene chloride at a temperature ranging from 10° C. to room temperature.

The reaction of a compound of formula (II) to produce a compound of formula (III) may be carried out with acetonitrile and a base such as sodium hydride in a suitable solvent such as diethylether, tetrahydrofuran, dioxane at a temperature ranging from room temperature to 120° C.

The reaction between a compound of formula (III) to produce a compound of formula (IV) is carried out with hydrazine hydrate, in a solvent such as methanol or ethanol at a temperature ranging from room temperature to 80° C.

The reaction of a compound of formula (IV) to produce a compound of formula (V) is carried out with oxone® (potassium peroxymonosulfate) or another oxidizing agent such as hydrogen peroxide in a suitable solvent such an a mixture of water-acetone at a temperature ranging from 0° C. to room temperature.

The reaction of a compound of compound of formula (V) to produce a compound of formula (VI) is carried out with tert-butoxycarbonyl anhydride in a suitable solvent such as mixture of methylene chloride-water at room temperature.

The reaction of a compound of formula (VI) to produce a compound of formula (VII) may be carried out directly with hydrogen in presence of a catalyst such as palladium on charcoal in a suitable solvent such as methanol or ethanol at room temperature.

Also, the optional conversion of a compound of formula (I) into another compound of formula (I) can be carried according to known methods.

The optional salification of a compound of formula (I) or the conversion of a salt into the free compound as well the separation of a mixture of isomers into the single isomers may be carried out by conventional methods.

A compound of formula (VIII) wherein X is hydroxy or a leaving group as defined above as well as the compound formula (II) are known or can be obtained according to conventional techniques.

When preparing the compounds of formula (I), optional functional groups within both the starting materials or the intermediates thereof, which could give rise to unwanted side reactions, are preferably protected according conventional techniques.

Likewise, the conversion of these protected compounds into the free deprotected compounds may be carried out according to well-known procedures.

Pharmacology

The compounds of formula (I) are active as cdk/cyclin ihibitors as they gave positive results when test according to the following procedure.

The inhibiting activity of putative cdk/cyclin inhibitors and the potency of selected compounds was determined through a method of assay based on the use of the MultiScreen-PH 96 well plate (Millipore), in which phosphocellulose filter paper was placed at each well bottom allowing binding of positive charged substrate after a washing/filtration step.

When a radioactivity labelled phosphate moiety was transferred by the ser/threo kinase to the filter-bound histone, light emitted was measured in a scintillation counter.

The inhibition assay of cdk2/Cyclin A activity performed according to the following protocol:

Kinase reaction: 1.5 •M histone H1 substrate, 25 •M ATP (0.5 uCi P33g-ATP), 100 ng Cyclin A/cdk2 complex, 10 •M inhibitor in a final volume of 100 •1 buffer (TRIS HCl 10 mM pH 7.5, $MgCl_2$ 10 mM, 7.5 mM DTT) were added to each well of a 96 U bottom well plate. After 10 min at 37° C. incubation, reaction was stopped by 20 •1 EDTA 120 mM.

Capture: 100·1 were transferred from each well MultiScreen plate, to allow substrate binding phosphocellulose filter. Plates were then washed 3 times with 150•1/well PBS $Ca^{++}/Mg^{++}$ free and filtered by MultiScreen filtration system.

Detections: filters were allowed to dry at 37° C., then 100 ·1/well scintillant were added and 33P labelled histone H1 was detected by radioactivity counting in the Top-Count instrument.

Results: data were analyzed and expressed as % inhibition referred to total activity of enzyme (=100%).

All compounds showing inhibition >50% were further analyzed in order to study and define the kinetic-profile of the inuibitor via Ki calculation.

The protocol used was the same described above, except for ATP and substrate concentrations. Either the concentate of ATP and histone H1 substrate were varied: 4,8, 12, 24, 48 •M for ATP (containing proportionally diluted P33g-ATP) and 0.4, 0.8, 1.2, 2.4, 4.8 •M for histone were used in absence and presence of two different, properly chosen inhibitor concentrations.

Experimental data were analyzed by the computer program "SigmaPlot" for Ki determination, using a random bireactant system equation:

$$v = \frac{Vmax \frac{(A)(B)}{aKAKB}}{1 + \frac{(A)}{KA} + \frac{(B)}{KB} + \frac{(A)(B)}{aKAKB}}$$

where A=ATP and B=histone H1.

In addition, the inhibiting activity of putative cdk/cyclin inhibitors and the potency of selected compounds was determined using a method of assay based on the use of a SPA (Scintillation Proximity Assay) 96 well plate assay. The assay is based on the ability of streptavidin-coated SPA beads to capture a biotinylated peptide derived from a phosphorylation site of histone.

When a radioactivity labelled phosphate moiety was transferred by the ser/threo kinase to the biotinylated histone peptide, light emitted was measured in scintillation counter.

the inhibition assay of cdk5/p25 activity was performed according to the following protocol;

Kinase reaction: 1.0 •M biotinylated histone peptide substrate, 0.25 uCi P33g-ATP, 4 nM cdk2/p25 complex, 0–100 •M] inhibitor in a final volume of 100 •1 buffer (Hepes 20 mM pH 7.5, $MgCl_2$ 15 mM, 1 mM DTT) were added to each well of a 96 U bottom well plate. After 20 min at 37° C. incubation, the reaction was stopped by the addition of 500 ug SPA beads in phosphate-buffered saline containing 0.1% Triton X-100, 50 µM ATP and 5 mM EDTA. The beads were allowed to settle, and the radioactivity incorporated in the 33P-labelled peptide was detected in a Top Count scintillation counter.

Results: Data were analyzed and expressed as % Inhibition using the formula:

$$100 \times (1-(Unknown-Bkgd)/(Enz.\ Control-Bkgd))$$

IC50 values were calculated using a variation of the four parameter logistics equation:

$$Y=100/[1+10\hat{}\{(LogEC50-X)*Slope\}]$$

Where X=log(uM) and Y=% Inhibition.

The compounds of formula (I) are therefore useful to restrict the unregulated proliferation of tumor cells, hence in therapy in the treatment of various tumors such as, for instance, carcinomas, e.g., mammary carcinoma, carcinoma, bladder carcinoma, colon carcinoma, ovary endometrial tumors, sarcomas, e.g., soft tissue and bone sarcomas, and the hematological malignancies such as, e.g., leukemias.

In addition, the compounds of formula (I) are also useful in the treatment of other cell proliferative disorders such as psoriasis, vascular smooth cell proliferation associated with atherosclerosis and post-surgical stenosis a restenosis, and in the treatment of Alzheimer's disease.

The compounds of the present invention can be administered either as single agents or, alternatively, in combination with known anticancer treatments such as radiation therapy or chemotherapy regimen in combination with cytostatic or cytotoxic agents.

As an example, the inventive compounds can be administered combination with one or more chemotherapeutic agents such as, for instance, taxane, taxane derivatives, CPT-11, camptothecin derivatives, anthracycline glycosides, e.g., doxorubicin or epirubicin, etoposide, navelbine, vinblastine, carboplatin, cisplatin and the like, optionally within liposomal formulations thereof.

The compounds of formula (I) of the present invention, suitable for administration to a mammal, e.g., to humans, can be administered by the usual routes and the dosage, level depends upon the age, weight, conditions of patient and the administration route.

For example, a suitable dosage adopted for oral administration of a compound of formula (I) may range from about 10 to about 500 mg per dose, from 1 to 5 times daily. The compounds of the invention can be administered in a variety of dosage forms, e.g., orally, in the form tablets, capsules, sugar or film coated tablets, liquid solutions or suspensions; rectally in the form supositories; parenterally, e.g.

intramuscularly, or intravenous and/or intrathecal and/or intraspinal injection or infusion.

The present invention also includes pharmaceutical compositions comprising a compound of formula (I) or a pharmaceutically acceptable salt thereof in association with a pharmaceutically acceptable excipient, which may be a carrier or a diluent.

The pharmaceutical compositions containing the compounds of the invention are usually prepared following convention methods and are administered in a pharmaceutically suitable form.

For example, the solid oral forms may contain, together with the active compound, diluents, e.g., lactose, dextrose saccharose, sucrose, cellulose, corn starch or potato starch; lubricants, e.g., silica, talc, stearic acid, magnesium or calcium stearate, and/or polyethylene glycols; binding agents, e.g., starches, arabic gum, gelatin methylcellulose, carboxymethylcellulose or polyvinyl pyrrolidone; disintegrating agents, e.g., a starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g, syrups, emulsions and suspensions.

The syrups may contain as carrier, for example, saccharose or saccharose with glycerine and/or mannitol and sorbitol.

The suspensions and the emulsions may contain as carrier, for example, a natural gum, agar, sodium alginate, pectin, methylcellulose, carboxymethylcellulose, or polyvinyl alcohol.

The suspension or solutions for intramuscular injections may contain, together with the active compound, a pharmaceutically acceptable carrier, e.g., sterile water, olive oil, ethyl oleate, glycols, e.g., propylene glycol, and, if desired, a suitable amount of lidocaine hydrochloride.

The solutions for intravenous injections or infusions may contain as a carrier, for example, sterile water or preferably they may be in the form of sterile, aqueous isotonic saline solutionsor they may contain as a carrier propylene glycol, The suppositories may contain together with the active compound a pharmaceutically acceptable carrier, e.g., cocoa butter, polyethylene glycol, a polyoxyethylene sorbitan fatty acid ester surfactant or lecithin

EXAMPLES

Having generally descnrbed this invention, a further understanding can be obtained by reference to certain specific examples which are provided herein for purposes of illustration only and are not intended to be limiting unless otherwise specified.

Example 1

N-(5-cycloproyyl-1H-pyrazol-3-yl)-2,2-diphenyl acetamide

To a solution of 45.6 mg (0.215 mmol) of diphenylacetic acid in 3 ml of dichloromethane at 0° C. 41.2 mg (0.215 mmol) of N-(3-dimethylaminopropyl)-N'-ethylcarbodiimide hydrochloride were added. After 1 hour at the same temperature under stirring 40 mg (0.179 mmol) of tert-butyl-3-amino-5-cyclopropyl-1H-pyrazole-1-carboxylate were added. The mixture was maintained at room temperature for 16 hours, then was diluted with dichloromethane and washed with a saturated solution of sodium hydrogenocarbonate. The organic layer was dried over anhydrous sodium sulfate evaporated to dryness, to give, after column chromatography (hexane-ethylacetate) 60 mg (80% yield) of N-(5-cyclopropyl-1-terbutoxycarbonyl-pyrazol-3-yl)-2,2-diphenyl acetamide. This intermediate was submitted to hydrolysis with 15 ml of trifluoroacetic acid 10% v/v in dichloromethane for an hour. The solvent was then evaporated under vacuum. the residue redissolved with dichloromethane and washed with a saturated solution sodium hydrogen carbonate. The organic layer was dried over anhydrous sodium sulfate and evaporated to give 42 mg (92% yield) of the title compound.

$^1$H-NMR (400 MHz, DMSO-$d_6$) δ ppm: 0.62 (m, 2H, cyclopropyl CH$\underline{H}$+C$\underline{H}$H); 0.88 (m, 2H, cyclopropyl C$\underline{H}$H+CH$\underline{H}$; 1.81 _(dddd, 1H, J=5.2, 5.2, 8.4, 8.4, cyclopropyl C$\underline{H}$); 5.17 (s, 1H, C$\underline{H}$Ph$_2$); 6.17 (s, 1H, pyrazole C$\underline{H}$); 7.30 (m, 10H, phenyl C$\underline{H}$); 10.6 (s, 1H, amidic N$\underline{H}$); 12.04 (s, 1H, pyrazole N$\underline{H}$).

ESI (+) MS: m/z 318 (100, MH+).

m.p. 218–220° C.

Analogously the following products can be prepared starting from the corresponding carboxylic acid:

N-(3-cyclopropyl-1H-pyrazol-5-yl)-2-(3-methoxyphenyl)acetamide m.p. 118–120° C.;

N-(3-cyclopropyl-1H-pyrazol-5-yl)-2-(4-nitrophenyl) acetamide m.p. 183–185° C.;

2-(1,3-benzodioxol-5-yl)-N-(3cyclopropyl-1H-pyrazol-5-yl)acetamide m.p. 174–176° C.

Example 2

2-(1,3-benzodioxol-5-yl)-N-(3-cyclopropyl-1H-pyrazol-5-yl)-acetamide

To a solution of 96.8 mg (0.537 mmol) of 2-(1,3-benzodioxol-5-yl)-acetic acid in 3 ml of dichloromethane 360 mg (0.720 mmol) of polystyrene supported dicyclohexylcarbodiimide (loading=2 mmol/g) and 40 mg (0.179 mmol) of tert-butyl-3-amino- 5-cyclopropyl-1H-pyrazole-1-carboxylate were added. The mixture was maintained under stirring at room temperature for 96 hours and after that time filtered, washed several times with dichloromethane and evaporated to dryness. The residue was re-dissolved with 3 ml of trifluoroacetic acid 10% V/V in dichloromethane and maintained at room temperature for an hour. The solvent was then evaporated, the residue re-dissolved in dichloromethane and washed with a saturated solution of sodium hydrogenocarbonate. The organic layer was evaporated to dryness to give, after trituration with diethylether, 32 mg (63% yield) of the title compound.

ESI (+) MS: m/z 286 (100, MH$^+$). m.p. 174–176° C.

Analogously, the following products can be prepared starting from the corresponding carboxylic acid:

N-(3-cyclopropyl-1H-pyrazol-5-yl)-2-[4-(dimethylamino)phenyl]acetamide;

N-(3-cyclopropyl-1H-pyrazol-5-yl)-1-phenylcyclopropancarboxamide;

N-(3-cyclopropyl-1H-pyrazol-5-yl)-2-(4-methoxyphenyl)acetamide;

N-(3-cyclopropyl-1H-pyrazol-5-yl)-2-phenylpropanamide;

N-(3-cyclopropyl-1H-pyrazol-5-yl)-2-(3,4-diethoxyphenyl)acetamide;

N-(3-cyclopropyl-1H-pyrazol-5-yl)2-(1H-indol-3-yl)acetamide;

N-(3-cyploroyl-1H-pyrazol-5-yl)-2-(5-methoxy-1H-indol-3-yl)acetamide;

N-(3-cycloprpy-1H-pyrazol-5-yl)-2-(1-metbyl-1H-indol-3-yl)acetamide;

2-(5-chloro-1-benzothiophen-3-yl)-N-(3yclopropyl-1H-pyrazol-5-yl)acetamide;

2-(1-benzothiophen-3-yl)-N-(3-cyclopropyl-1H-pyrazol-5-yl)acetamide;

N-(3-cyclopropyl-1H-pyrazol-5-yl)-3-cyclopentylpropanamide;

2-(4chlorophenyl)-N-(3-cyclopropyl-1H-pyrazol-5-yl)acetamide;

N-(3-cyclopropyl-1H-pyrazol-5-yl)-4-oxo-4-phenylbutanamide;

3-cyclopropyl-1H-pyrazol-5-yl)-2-(2,3-dihydro-1H-inden-5-yl)acetamide;

3-(2-chlorophenoxy)-N-(3-cyclopropyl-1H-pyrazol-5-yl)propanamide;

N-(3-cyclopropyl-1H-pyrazol-5-yl)-2-oxo-2-phenylacetamide;

N-(3-cyclopropyl-1H-pyrazol-5-yl)-2-(4methylphenyl)acetamide;

2-[1,1'-biphenyl]-4-yl-N-(3-cyclopropyl-1H-pyrazol-5-yl)acetamide;

N-(3-cyclopropyl-1H-pyrazol-5-yl)-2-(3-chlorophenyl)acetamide;

N-(3-cyclopropyl-1H-pyrazol-5-yl)-2-(1-naphthyl)acetamide;

N-(3-cyclopropyl-1H-pyrazol-5-yl)-2-(2-fluorophenyl)acetamide;

N-(3-cyclopropyl- 1H-pyrazol-5-yl)-2-(2-chlorophenyl)acetamide;

N-(3-cyclopropyl-1H-pyrazol-5-yl)-2-(4-fluorophenyl)acetamide;

N-(3-cyclopropyl-1H-pyrazol-5-yl)-2-(4-trifluoromethylphenyl)acetamide;

N-(3-cyclopropyl-1H-pyrazol-5-yl)-2-methoxy-2-phenylacetamide;

N-(3-cyclopropyl-1H-pyrazol-5-yl)-3-oxo-1-indanecarboxamide;

N-(3-cyclopropyl-1H-pyrazol-5-yl)-2-(3-thienyl)acetamide;

N-(3-cyclopropyl-1H-pyrazol-5-yl)bicyclo[4.2.0]octa-1,3,5-triene-7-carboxamide;

N-(3-cyclopropyl-1H-pyrazol-5-yl)-4-phenyl-3-butenamide.

All compounds were characterized by mass spectrometry (MS). LC-MS confirmed that in each case the principle component had a molecular ion corresponding to the expected product. The compounds showed an HPLC area % ranging from 78 to 100.

HPLC analysis:
Solvent A: $H_2O/CH_3CN=90/10+0.1\%$ TFA
Solvent B: $H_2O/CH_3CN=10/90+0.075\%$ TFA

| Time (min) | % A | % B |
|---|---|---|
| 0 | 0 | 100 |
| 6.5 | 0 | 100 |
| 7 | 100 | 0 |
| 10 | 100 | 0 |

Rate: 1.5 ml/min
Detection: UV 254 nm
Temperature: room temperature
Column: Supelco™, Discovery RP Amide C16, 5 •m, (50×4.6)mm Example 3

3-Cyclopropyl-3-oxo-propanenitrile 4.5 g (0.15 mol) of sodium hydride 80% were suspended in 200 ml of dioxane, 7.5 ml of acetonitrile (0.15 mol) were dropped and, afier 20 minutes, a solution of ethyl cyclopropancarboxylate (0.125 mol) in 100 ml of the same solvent was added. The mixture was maintained at reflux for 3 hours, under stirring, then 400 ml of water were added and the unreacted starting material extracted with methylene chloride. The aqueous layer was acidified with diluted hydrochloric acid and extracted with the same solvent. The organic layer was dried over anhydrous sodium sulfate and evaporated to dryness to give a residue that, after column chromatography (cyclohexane-ethylacetate), afforded 7.8 g (57% yield) of the title compound.

$^1$H-NMR (400 MHz, CDCl$_3$) δ ppm: 1.20 (m, 2H, cyclopropyl C$\underline{H}$H+CH$\underline{H}$); 1.21 (m, 2H, CH$\underline{H}$+C$\underline{H}$N; 2.12 (dddd, 1H, J=7.6, 7.6, 4.5, 4.5, cyclopropyl C$\underline{H}$); 3.59 (s, 2H, COC$\underline{H}_2$).

EI-MS: m/z 69 (85, M-C$_3$H$_5^-$); m/z 39 (100, C$_3$H$_5^+$).

Example 4

3-Cyclopropyl-5-amino-1H-pyrazole 5 g (0.046 mol) of 3cyclopropyl-3-oxo-propanenitrile were dissolved in 200 ml of ethanol and 2.26 ml (0.046 mol) of hydrazine hydrate were added. The solution was maintained at reflux for 5 hours and then the solvent evaporated under vacuum. The residue was re-dissolved with methylene chloride and washed several times with brine. The organic layer was dried over anhydrous sodium sulfate and the solvent evaporated to give 4.53 g (80% yield) of the title compound.

$^1$H-NMR (400 MHz, DMSO-d$_6$) δ ppm: 0.54 (m, 2H, pyrazole C$\underline{H}$H+CH$\underline{H}$); 0,76 (m, 2H, CH$\underline{H}$+C$\underline{H}$H); 1.68 (dddd, 1H, J=4.9, 4.9, 8.3, 8.3, pyrazole C$\underline{H}$); 5.02 (s, 1H, pyrazole CH); 6–7 (b, 3H, NH+NH$_2$).

ESI (+)MS: m/z 124 (100, MH$^+$).

Example 5

3-Cyclopropyl-5-nitro-1H-pyrazole

To a solution of 2.7 g of sodium hydrate in 454 ml of water 7.1 g (0.058 mol) of 3-cyclopropyl-5-amino-1H-pyrazole and 46.5 g of sodium hydrogenocarbonate were added at 0° C. After 10 minutes a solution of 337 ml of acetone in 221 ml of water and a solution of 130 g (0.21 mol) of oxone in 580 ml of water were contemporaneously dropped under vigorous stirring. After 4 hours at the same temperature the reaction is quenched with a saturated solution of sodium sulfite and extracted with ethylacetate. The organic layer was dried over anhydrous sodium sulfate and evaporated to dryness to give 4.6 g (52% yield) of the title compound.

$^1$H-NMR (400 MHz, CDCl$_3$) δ ppm: 0.79 (m, 2H, cyclopropyl CHH+CHH; 1.10 (m, 2H, cyclopropyl CHH+CHH); 2.01 (dddd, 1H, J=5.1, 5.1, 8.2, 8.2, cyclopropyl CH); 6.51 (s, 1H, pyrazole CH).

EI-MS: m/z 153 (100, M$^+$); 136 (60, M-OH).

Example 6

Tert-butyl-3-nitro-5-cyclopropyl-1H-pyrazole-1-carboxylate 4.9 g (0.032 mol) of 3-cyclopropyl-5-nitro-1H-pyrazole were dissolved in 200 ml of methylene chloride and 200 ml of a saturated solution of sodium hydrogenocarbonate were added. 35 g (0.16 mol) of tertbutoxycarbonyl anhydride were then added under stirring at room temperature. After 24 hours the layers were separated and the organic one dried over sodium sulfate and evaporated under vacuum. The residue was chromatographed on a silica gel column (cyclohexane-ethyl acetate) to give 7.7 g (95% yield) of the title compound.

$^1$H-NMR (400 MHz, CDCl$_3$) δ ppm: 0.78 (m, 2H, cyclopropyl CHH+CHH); 1.13 (m, 2H, CHH+CHH); 1.68 (s, 9H, (CH$_3$)$_3$—); 2.48 (dddd, 1H, J=5.3, 5.3, 8.5, 8.5, cyclopropyl CH); 6.49 (s, 1H, pyrazole CH).

ESI (+) MS: m/z 276 (100, MNa$^+$); 220 [60, (MNa—C$_4$H$_8$.)$^+$].

Example 7

Tert-butyl-3-amine-5cyclopropyl-1H-pyrazole-1-carboxylate 1.2 g (4.74 mmol) of tert-butyl-3-nitro-5-cyclopropyl-1H-pyrazole-1-carboxylate were dissolved in 20 ml of ethanol and hydrogenated in presence of 200 mg of palladium on charcoal (10%) at 50 psi and room temperature to give, after filtration celite and evaporation of the solvent, 0.96 g (95% yield) of the title compound.

$^1$H-NMR (400 MHz, CDCl$_3$) δ ppm: (m, 2H, cyclopropyl CHN+CHH); 0.97 (m, 2H cyclopropyl CHH+CHH); 1.63 (s, 9H, (CH$_3$)$_3$—); 2.34 (dddd, 1H, J=5.2, 5.2, 8.4, 8.4, cyclopropyl CH); 3.82 (s b, 2H, NH$_2$); 5.39 (s, 1H, pyrazole CH). ESI (+) MS: m/z 246 (20, MNa$^+$); 168 [100, (MH—C$_4$H$_8$)$^+$]; 124 [90, [MH—C$_5$H$_8$O$_2$)$^+$].

Example 8

N-(3-cyclopropyl-1H-pyrazol-5-yl)-benzamide

To a solution of 0.37 g (3 mmol) of 3-cyclopropyl-5-amino-1H-pyrazole in 15 ml of dichloromethane 0.8 ml (7.3 mmol) of N-methylmorpholine and 0.8 ml (6.9 mmol) of benzoyl chloride were successively added at room temperature. After 16 hours under stirring the mixture was concentrated and the residue was dissolved in 15 ml of methanol. 3.5 ml of sodium hydrate 2.5 M were added dropwise and 10 ml of tetrahydrofuran were finally added in order to obtain a homogeneous solution. After 15 minutes the mixture was concentrated and poured into water. The precipitate was filtered and dried in vacuum to afford 585 mg (86% yield) the title compound.

m.p. 234° C.;

$^1$H NMR (DMSO-d$_6$) δ ppm 12.1 (s, 1H), 10.65 (s, 1H), 7.97 (app.d, 2H), 7.7 (m, 3H), 6.31 (s, 1H), 1.89 (m, 1H), 0.93 (m, 2H), 0.69 (m, 2H);

MS (EI) m/z (rel. intensity) 227 (M$^+$, 22), 226 (11), 199 (23), 106 (13), 105 (95), 78 (11), 77 (99), 66 (9), 65 (14), 51 (29).

Analogously the following products can be prepared startng from the corresponding carboxylic acid:

N-(3-cyclopropyl-1H-pyrazol-5-yl)-4-chlorobenzamide
m.p. 186–187° C.;
$^1$H NMR (DMSO-d$_6$) δ ppm 12.2 (s, 1H), 10.8 (s, 1H), 7.97 (app.d, 2H), 7.53 (app.d, 2H), 6.28 (s, 1H), 1.87 (m, 1H), 0.91 (m, 2H), 0.67 (m, 2H);
MS (EI) m/z (rel. intensity) 261 (M$^+$, 27), 235 (8), 233 (36), 141 (66), 139 (99), 113 (31), 111 (78), 65 (10).

N-(3-cyclopropyl-1H-pyrazol-5-yl)-4-phenylbenzamide
m.p. 253–254° C.;
$^1$H NMR (DMSO-d$_6$) δ ppm 12.15 (s, 1H), 10.7 (s, 1H), 8.05 (d, J=8 Hz, 2H), 7.76 (d, J=8 Hz, 2H), 7.72 (d, J=7 Hz, 2H), 7.48 (t, J=7 Hz, 2H), 7.39 (t, J=7 Hz, 1H), 6.31 (br s, 1H), 1.88 (m, 1H), 0.91 (m, 2H), 0.68 (m, 2H);
MS (FAB) m/z (rel. intensity) 304 (MH$^+$, 83), 152 (34), 151 (47), 128 (36), 107 (50), 95 (38), 89 (32), 78 (27), 77 (99), 39 (35).

N-(3-cyclopropyl-1H-pyrazol-5-yl)phenylacetamide
m.p. 208° C.;
$^1$H NMR (DMSO-d$_6$) δ ppm 12.05 (s, 1H), 10.5 (s, 1H), 7.28 (app.d, 4H), 7.21 (m, 1H), 6.10 (s, 1H), 3.54 (s, 2H) 1.80 (m, 1H), 0.86 (m, 2H), 0.59 (m, 2H);
MS (EI) m/z (rel. intensity) 241 (M$^+$, 64), 123 (99), 118 (10), 96 (16), 95 (9), 91 (99), 80 (35), 73 (14), 66 (10), 65 (48).

N-(3-cyclopropyl-1H-pyrazol-5-yl)-3-phenylpropanamide
m.p. 152–160° C.,
$^1$H NMR (DMSO-d$_6$) δ ppm 12.00 (br s, 1H), 10.25 (s, 1H), 7.21 (m, 5H), 6.12 (s, 1H), 2.83 (t, J=8 Hz, 2H), 2.53 (t, J=8 Hz, 2H) 1.82 (m, 1H), 0.87 (m, 2H), 0.61 (m, 2H);
MS (FAB) m/z (rel. intensity) 256 (MH$^+$, 99), 255 (18), 219 (15), 167 (9), 150 (9), 135 (10), 107 (26), 105 (23), 93 (9), 89 (28).

N-(3-cyclopropyl-1H-pyrazol-5-yl)-1-benzothiophene-2-carboxamide
m.p. 238–239° C.;
$^1$H NMR (DMSO-d$_6$) δ ppm 12.2 (s, 1H), 11.1 (s, 1H), 8.39 (s, 1H), 8.01 (app.d, 1H), 7.91 (app.d, 1H), 7.44 (m, 2H), 6.28 (s, 1H), 1.88 (m, 1H), 0.91 (m, 2H), 0.67 (m, 2H);
MS (EI) m/z (rel. intensity) 283 (M$^+$, 78), 255 (18), 162 (23), 161 (99), 133 (75), 89 (93), 73 (18), 65 (14), 63 (11).

Example 9

N-(3-cyclopropyl-1H-pyrazol-5-yl)-4-bromobenzemide 122 mg (loading 1.91 mmol/g, 0.233 mmol) of polystyrene supported-N-methylmorpholine were suspended in 4 ml of chloromethane and then treated with 25.6 mg (0.117 mmol) of 4-bromobenzoyl chloride followed by 4.8 mg (0.039 mmol) of 3-cyclopropyl-5-amino-pyrazole. After 48 hours under stirring at room temperature the resin was separated by filtration and washed with 2 ml of dichloromethane. The filtrate was evaporated to dryness, the residue re-dissolved in 4 ml of dichloromethane and 100 mg of polystyrene supported trisamine were added. After 48 hours or stirring at room temperature the resin was filtered, washed with 2 ml of dichloromethane and concentrated to give, after triturating with diethylether, 9.3 mg (78% yield) of the title compound.

Analogously, the following products can be prepared starting from the corresponding acid chloride:

N-(3-cyclopropyl-1H-pyrazol-5-yl)-3,5-ditrifluoromethylbenzamide;
N-(3-cyclopropyl-1H-pyrazol-5-yl)-3,3-dimethylbutanamide;
N-(3-cyclopropyl-1H-pyrazol-5-yl)4-iodobenzamide;
N-(3-cyclopropyl-1H-pyrazol-5-yl)-1-naphtamide;
N-(3-cyclopropyl-1H-pyrazol-5-yl)-3-cyanobenzamide;
N-(3-cyclopropyl-1H-pyrazol-5-yl)-1,3-benzodioxol-5-carboxamide;
N-(3-cyclopropyl-1H-pyrazol-5-yl)-4-morpholinocarboxamide;
(E)-3-(2-chlorophenyl)-N-(3-cyclopropyl-1H-pyrazol-5-yl)-2-propenamide;
N-(3-cyclopropyl-1H-pyrazol-5-yl)-2-(propylsulfanyl)-nicotinamide;
N-(3-cyclopropyl-1H-pyrazol-5-yl)-2,2,5,7-tetramethyl-1-1-oxo4-indanecarboxamide;
N-(3-cyclopropyl-1H-pyrazol-5-yl)-2-pyridinecarboxamide;
N-(3-cyclopropyl-1H-pyrazol-5-yl)-2-adamantanecaboxamide;
N-(3-cyclopropyl-1H-pyrazol-5-yl)-4-methylbenzamide;
N-(3-cyclopropyl-1H-pyrazol-5-yl)-2,4-difluoromethylbenzamide;
N-(3-cyclopropyl-1H-pyrazol-5-yl)-2-chlorobenzamide;
N-(3-cyclopropyl-1H-pyrazol-5-yl)-2,4-dichlorobenzamide;
N-(3-cyclopropyl-1H-pyrazol-5-yl)-2,6-dichlorobenzamide;
N-(3-cyclopropyl-1H-pyrazol-5-yl)-2-methoxybenzamide;
N-(3-cyclopropyl-1H-pyrazol-5-yl)-2-methylbenzamide;
N-(3-cyclopropyl-1H-pyrazol-5-yl)-3-fluorobenzamide;
N-(3-cyclopropyl-1H-pyrazol-5-yl)-3-chlorobenzamide;
N-(3-cyclopropyl-1H-pyrazol-5-yl)-3,5-dimethoxybenzamide
N-(3-cyclopropyl-1H-pyrazol-5-yl)-3-methylbenzamide;
N-(3-cyclopropyl-1H-pyrazol-5-yl)-4-fluorobenzamide;
N-(3-cyclopropyl-1H-pyzrazol-5-yl)-4-trifluoromethylbenzamide;
Methyl-4-[(3-cyclopropyl-1H-pyrazol-5-yl)-amino-]-4-oxobutanoate;
N-(3-cyclopropyl-1H-pyrazol-5-yl)-cyclopropancarboxamide;
N-(3-cyclopropyl-1H-pyrazol-5-yl)-4-cyanobenzamide;
N-(3-cyclopropyl-1H-pyrazol-5-yl)-2-naphthamide;
N-(3-cyclopropyl-1H-pyrazol-5-yl)-2-thiphenecarboxamide;
N-(3-cyclopropyl-1H-pyrazol-5-yl)-2-quinoxalinecarboxamide;
N-(3-cyclopropyl-1H-pyrazol-5-yl)-3,4-difluorobenzamide;
N-(3-cyclopropyl-1-pyrazol-5-yl)-3,5-difluorobenzamide;
N-(3-cyclopropyl-1H-pyrazol-5-yl)-2-(2,5-dimethoxyphenyl)acetamide;
2-(4-chlorophenoxy)-N-(3-cyclopropyl-1H-pyrazol-5-yl)-nicotinamide;
3-chloro-N-(3-cyclopropyl-1H-pyrazol-5-yl)-2-thiophenecarboxamide;
2,5-dichloro-N-(3-cyclopropyl-1H-pyrazol-5-yl)-3-thiophenecarboxamide;
N-(3-cyclopropyl-1H-pyrazol-5-yl)-2-(3-methoxyphenyl)acetamide;
N-(3-cyclopropyl-1H-pyrazol-5-yl)-2-ethoxybenzamide;
N-(3-cyclopropyl-1H-pyrazol-5-yl)-2,4-dimethoxybenzmide;
N-(3-cyclopropyl-1H-pyrazol-5-yl)-2-phenylbutanamide;
N-(3-cyclopropyl-1H-pyrazol-5-yl)-4-trifluoromethoxybenzamide;
3-chloro-N-(3-cyclopropyl-1H-pyrazol-5-yl)-benzo[b]thiophene-2-carboxamide.

All compounds were characterzed by mass spectrometry (MS). LC-MS confirmed that in each case the principle component had a molecular ion corresponding to the expected product. The compounds showed an HPLC area % ranging from 70 to 100.

HPLC analysis:
Solvent A: $H_2O/CH_3CN=90/10+0.1\%$ TFA
Solvent B: $H_2O/CH_3CN=10/90+0.075\%$ TFA

| Time (min) | % A | % B |
|---|---|---|
| 0 | 0 | 100 |
| 6.5 | 0 | 100 |
| 7 | 100 | 0 |
| 10 | 100 | 0 |

Rate: 1.5 ml/min
Deteton: W 254 nm
Temperature: room temperature
Column: Supelco™, Discovery RP Amide C16, 5 •m, (50×4.6)mm Obviously, numerous modifications and variations of the present invention are possible in light of the above teachings. It is therefore to be understood that within the scope of the appended claims, the invention may be practiced otherwise than as specifically described herein.

What is claimed is:

1. A method of treating cell proliferative disorders associated with an altered cell dependent kinase activity, comprising:
    administering to a mammal in need thereof an effective amount of a compound represented by formula (I):

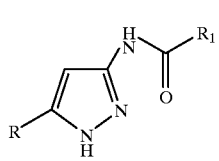

(I)

wherein
    R is a $C_3$–$C_6$ cycloalkyl group optionally substituted with a straight or branched $C_1$–$C_6$ alkyl group; and
    $R_1$ is a straight or branched $C_1$–$C_6$ alkyl, $C_2$–$C_4$ alkenyl, cycloalkyl, aryl, arylalkyl, arylcarbonyl, aryloxyalkyl or arylalkenyl group, which is optionally substituted with one or more groups selected from the group consisting of cycloalkyl, hydroxy, alkylthio, alkoxy, amino, alkylamino, dialkylamino, alkoxycarbonylamino, alkoxycarbonylalkylamino, alkylcarbonyl, alkylsulphonyl, alkoxycarbonyl, carboxy, halogen, nitro, aryloxy, arylthio, arylsulphonyl, N-alkyl-piperazinyl, piperidinyl, 4-morpholinyl, arylamino, cyano, alkyl, aryl, oxo, haloaryl, haloarylalkyl, haloaryloxy, haloarylsulphonyl, aminosulphonyl, aminocarbonyl, arylcabonyl, perfluorinated alkyl, and perfluorinated alkoxy groups;

or a pharmaceutically acceptable salt thereof.

2. The method of claim 1, wherein the cell proliferative disorder is selected from the group consisting of cancer, Alzheimer's disease, vial infections, auto-immune diseases and neurodegenerative disorders.

3. The method of claim 2, wherein the cancer is selected from the group consisting of carcinoma, squamous cell carcinoma, hematopoietic tumors of myeloid or lymphoid lineage, tumors of mesenchymal origin, tumors of the central and peripheral nervous system, melanoma, seminoma, teratocarcinoma, osteosarcoma, xenoderoma pigmentosum, keratoctanthoma, thyroid follicular cancer and Kaposi's sarcoma.

4. The method of claim 1, wherein the cell proliferative disorder is selected from the group consisting of benign prostate hyperplasia, familial adenomatosis polyposis, neuro-fibromatosis, psoriasis, vascular smooth cell proliferation associated with atherosclerosis, pulmonary fibrosis, arthritis glomerulonephritis and post-surgical stenosis and restenosis.

5. The method of claim 1, which provides tumor angiogenesis and metastasis inhibition.

6. The method of claim 1, which provides cell cycle inhibition or cdk/cyclin dependent inhibition.

7. The method of claim 1, further comprising subjecting the mammal in need thereof to a radiation therapy or chemotherapy regimen in combination with at least one cytostatic or cytotoxic agent.

8. The method of claim 1, wherein the mammal in need thereof is a human.

9. The method of claim 1, wherein R is a cycloalkyl group and $R_1$ is a $C_1-C_4$ alkyl, phenyl, phenylalkyl, or 5 or 6 membered heteroaryl or heteroarylalkyl group, which is optionally further substituted with said groups.

10. The method of claim 1, wherein R is a cycloalkyl group and $R_1$ is a $C_1-C_4$ alkyl, phenyl or phenylalkyl group, which is optionally substituted with hydroxy, halogen, amino, alky, alkoxy, alkoxycarbonyl, phenyl or by an optionally benzocondensed heterocycle.

11. A 3-amino-pyrazole derivative represented by formula (I):

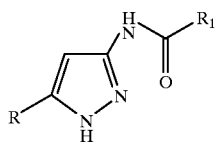

wherein
R is a $C_3-C_5$ cycloalkyl group optionally substituted by a straight or branched $C_1-C_6$ alkyl group;
$R_1$ is a straight or branched $C_1-C_6$ alkyl group, $C_2-C_4$ alkenyl, cycloalkyl, aryl, arylalkyl, arylcarbonyl, aryloxyalkyl or arylalkenyl group, which is optionally substituted with one or more groups selected from the group consisting of cycloalkyl, hydroxy, alkylthio, alkoxy, amino, alkylamino, dialkylamino, alkoxycarbonylamino, alkoxycarbonylalkylamino, alkylcarbonyl, alkylsulphonyl, alkoxycarbonyl, carboxy, halogen, nitro, aryloxy, arylthio, arylsulphonyl, N-alkyl-piperazinyl, piperidinyl, 4-morpholinyl, arylamino, cyano, alkyl, aryl, oxo, haloaryl, haloarylalkyl, haloaryloxy, haloarylsulphonyl, aminosulphonyl, aminocarbonyl, arylcarbonyl, perfluorinated alkyl, and perfluorinated alkoxy groups;

or a pharmaceutically acceptable salt thereof.

12. The 3-amino-pyrazole derivative of claim 11, wherein the aryl group is a phenyl, 1-naphtyl, 2-naphthyl, indanyl, indenyl, biphenyl, benzocycloalkyl, benzoheterocyclyl, quinoxalyl, indolyl or optionally benzocondensed pyrrolyl, furyl, thienyl, imidazolyl, pyrazolyl, thiazolyl, oxazolyl, isoxazolyl, pyridyl, pyrazinyl or pyrimidyl group.

13. The 3-amino-pyrazole derivative of claim 11, wherein R is a cycloalkyl group and $R_1$ is a $C_1-C_4$ alkyl, phenyl, phenylalkyl, or 5 or 6 membered heteroaryl or heteroarylalkyl group, which is optionally further substituted with said groups.

14. The 3-amino-pyrazole derivative of claim 11, wherein R is a cycloalkyl group and $R_1$ is a $C_1-C_4$ alkyl, phenyl or phenylalkyl group, which is optionally substituted with hydroxy, halogen, amino, alky, alkoxy, alkoxycarbonyl, phenyl or by an optionally benzocondensed heterocycle.

15. The 3-amino-pyrazole derivative of claim 14, wherein the optionally benzocondensed heterocycle is pyridine, pyrrole, thiophene, thiazole, isoxazole, furan, piperidine or morpholine.

16. The 3-amino-pyrazole derivative of claim 14, which is selected from the group consisting of:

N-(5-cyclopropyl-1H-pyrazol-3-yl)-2,2-diphenylacetamide;

N-(3-cyclopropyl-1H-pyrazol-5-yl)-2-(4-nitrophenyl)acetamide;

N-(3-cyclopropyl-1H-pyrazol-5-yl)-4-methoxybenzamide,

N-(3-cyclopropyl-1H-pyrazol-5-yl)-2-(3-methoxyphenyl)acetamide;

N-(3-cyclopropyl-1H-pyrazol-5-yl)-2-[4-(dimethylamino)phenyl]acetamide;

N-(3-cyclopropyl-1H-pyrazol-5-yl)-1-phenylcyclopropancarboxamide;

2-(1,3-benzodioxol-5-yl)-N-(3-cyclopropyl-1H-pyrazol-5-yl)acetamide;

N-(3-cyclopropyl-1H-pyrazol-5-yl)-2-(4-methoxyphenyl)acetamide;

N-(3-cyclopropyl-1H-pyrazol-5-yl)-2-phenylpropanamide;

N-(3-cyclopropyl-1H-pyrazol-5-yl)-2-(3,4-dimethoxyphenyl)acetamide;

N-(3-cyclopropyl-1H-pyrazol-5-yl)-2-(1H-indol-3-yl)acetamide;

N-(3-cyclopropyl-1H-pyrazol-5-yl)-2-(5-methoxy-1H-indol-3-yl)acetamide;

N-(3-cyclopropyl-1H-pyrazol-5-yl)-2-(1-methyl-1H-indol-3-yl)acetamide;

2-(5-chloro-1-benzothiophen-3-yl)-N-(3-cyclopropyl-1H-pyrazol-5-yl)acetamide;

2-(1-benzothiophen-3-yl)-N-(3-cyclopropyl-1H-pyrazol-5-yl)acetamide;

N-(3-cyclopropyl-1H-pyrazol-5-yl)-3-cyclopentylpropanamide;
2-(4-chlorophenyl)-N-(3-cyclopropyl-1H-pyrazol-5-yl)acetamide;
N-(3-cyclopropyl-1H-pyrazol-5-yl)-4-oxo-4-phenylbutanamide;
N-(3-cyclopropyl-1H-pyrazol-5-yl)-2-(2,3-diydro-1H-inden-5-yl)acetamide;
3-(2-chlorophenoxy)-N-(3-cyclopropyl-1H-pyrazol-5-yl)propanamide;
N-(3-cyclopropyl-1H-pyrazol-5-yl)-2-oxo-2-phenylacetamide;
N-(3-cyclopropyl-1H-pyrazol-5-yl)-2-(4-methylphenyl)acetamide;
2-[1,1'-biphenyl]-4-yl-N-(3-cyclopropyl-1H-pyrazol-5-yl)acetamide;
N-(3-cyclopropyl-1H-pyrazol-5-yl)-2-(3-chlorophenyl)acetamide;
N-(3-cyclopropyl-1H-pyrazol-5-yl)-2-(1-naphtyl)acetamide;
N-(3-cyclopropyl-1H-pyrazol-5-yl)-2-(2-fluorophenyl)acetamide;
N-(3-cyclopropyl-1H-pyrazol-5-yl)-2-(2-chlorophenyl)acetamide;
N-(3-cyclopropyl-1H-pyrazol-5-yl)-2-(4-fluorophenyl)acetamide;
N-(3-cyclopropyl-1H-pyrazol-5-yl)-2-(4-trifluoromethylphenyl)acetamide;
N-(3-cyclopropyl-1H-pyrazol-5-yl)-2-methoxy-2-phenylacetamide;
N-(3-cyclopropyl-1H~pyrazol-5-yl)-3-oxo-1-indanecarboxamide;
N-(3-cyclopropyl-1H-pyrazol-5-yl)-2-(3-thienyl)acetamide;
N-(3-cyclopropyl-1H-pyrazol-5-yl)bicyclo[4.2.0]octa-1.3,5-triene-7-carboxamide;
N-(3-cyclopropy-1H-pyrazol-5-yl)-4-phenyl-3-butenamide;
5-[(4-chlorophenyl)sulphonyl]-N-(5-cyclopropyl-1H-pyrazol-3-yl)-3-methyl-2-thiophenecarboxamide;
N-(5-cyclopropyl-1H-pyrazol-3-yl)-4-phenoxybenzamide;
4-bromo-N-(5-cyclobutyl-1H-pyrazol-3-yl)benzamide;
N-(5-cyclopropyl-1H-pyrazol-3-yl)-3,5-bis(trifluoromethyl)benzamide;
N-(5-cyclopropyl-1H-pyrazol-3-yl)-4-bromobenzamide;
N-(5-cyclopropyl-1H-pyrazol-3-yl)-3,3-dimethylbutanamide;
N-(5-cyclopropyl-1H-pyrazol-3-yl)-4-iodobenzamide;
N-(5-cyclopropyl-1H-pyrazol-3-yl)-1-napthamide;
N-(5-cyclopropyl-1H-pyrazol-3-yl)-3-cyanobenzamide;
N-(5-cyclopropyl-1H-pyrazol-3-yl)-1,3-benzadioxole-5-carboxamide;
3-(2-chlorophenyl)-N-(5-cyclopropyl-1H-pyrazol-3-yl)-2-propenamide;
2,5-dichloro-N-(5-cyclopropyl-1H-pyrazol-3-yl)-3-thiophenecarboxamide;
N-(5-cyclopropyl-1H-pyrazol-3-yl)-2-(propylsulfanyl)nicotinamide;
N-(5-cyclopropyl-1H-pyrazol-3-yl)-2,2,5,7-tetraethyl-1-oxo-4-indanecarboxamide;
N-(5-cyclopropyl-1H-pyrazol-3-yl)-2-pyridinecarboxamide;
N-(5-cyclopropy-1H-pyrazol-3-yl)-2-adamantanecarboxamide;
N-(5-cyclopropyl-1H-pyrazol-3-yl)-4-methylbenzamide;
N-(5-cyclopropyl-1H-pyrazol-3-yl)-2,3,4,5,6-pentafluorobenzamide;
N-(5-cyclopropyl-1H-pyrazol-3-yl)-2-phenoxyacetamide;
N-(5-cyclopropyl-1H-pyrazol-3-yl)-2-phenylacetamide;
N-(5-cyclopropyl-1H-pyrazol-3-yl)cyclopentancarboxamide;
N-(5-cyclopropyl-1H-pyrazol-3-yl)-2-(2-thienyl)acetamide;
N-(5-cyclopropyl-1H-pyrazol-3-yl)-3,5-dichlorobenzamide;
2-chloro-N-(5-cyclopropy-1H-pyrazol-3-yl)-6-methylisonicotinamide;
N-(5-cyclopropyl-1H-pyrazol-3-yl)-5-isoxazolecarboxamide;
2,4-dichloro-N-(5-cyclopropyl-1H-pyrazol-3-yl)-5-fluorobenzamide;
N-(5-cyclopropyl-1H-pyrazol-3-yl)-2,4-difluorobenzemide;
N-(5-cyclopropyl-1H-pyrazol-3-yl)-2-chlorobenzamide;
N-(5-cyclopropyl-1H-pyrazol-3-yl)-2,4-dichlorobenzamide;
N-(5-cyclopropyl-1H-pyrazol-3-yl)-2,6-dichlorobenzamide;
N-(5-cyclopropyl-1H-pyrazol-3-yl)-2-methoxybenzamide;
N-(5-cyclopropyl-1H-pyrazol-3-yl)-2-methylbenzamide;
N-(5-cyclopropyl-1H-pyrazol-3-yl)-3-fluorobenzamide;
N-(5-cyclopropyl-1H-pyrazol-3-yl)-3-chlorobenzamide;
N-(5-cyclopropyl-1H-pyrazol-3-yl)-3,5-dimethoxybenzamide;
N-(5-cyclopropyl-1H-pyrazol-3-yl)-3-methylbenzamide;
N-(5-cyclopropyl-1H-pyrazol-3-yl)-4-fluorobenzamide;
N-(5-cyclopropyl-1H-pyrazol-3-yl)-4-trifluoromethylbenzamide;
Methyl 4-[(5-cyclopropyl-1H-pyrazol-3-yl)amino]-4-oxobutanoate;
N-(5-cyclopropyl-1H-pyrazol-3-yl)cyclopropanecarboxamide;
N-(5-cyclopropyl-1H-pyrazol-3-yl)-4-cyanobenzamide,
N-(5-cyclopropyl-1H-pyrazol-3-yl)-2-napthamide;
N-(5-cyclopropyl-1H-pyrazol-3-yl)-2-thiophenecarboxamide;
N-(5-cyclopropyl-1H-pyrazol-3-yl)-2-quinoxalinecarboxamide;
N-(5-cyclopropyl-1H-pyrazol-3-yl)-3,4-difluorobenzarmide;
N-(5-cyclopropyl-1H-pyrazol-3-yl)-3,5-difluorobenzamide;
N-(5-cyclopropyl-1H-pyrazol-3-yl)-3,5-dimethoxybenzamide;
N-(5-cyclopropyl-1H-pyrazol-3-yl)-2-(2,5-dimethoxyphenyl)acetamide;
N-(5-cyclopropyl-1H-pyrazol-3-yl)-2-ethoxybenzamide;
N-(5-cyclopropyl-1H-pyrazol-3-yl)-3,4-dimethoxybenzamide;

N-(5-cyclopropyl-1H-pyrazol-3-yl)-2-phenylbutanamide;
N-(5-cyclopropyl-1H-pyrazol-3-yl)-4-(trifluoromethoxy) benzamide;
3-chloro-N-(5-cyclopropyl-1H-pyrazol-3-yl)-1-benzothiophene-2-carboxamide;
2-(4-chlorophenoxy)-N-(5-cyclopropyl-1H-pyrazol-3-yl) nicotinamide;
3-chloro-N-(5-cyclopropyl-1H-pyrazol-3-yl)-2-thiophenecarboxamide;
N-(3-cyclopropyl-1H-pyrazol-5-yl)acetamide;
N-(3-cyclopropyl-1H-pyrazol-5-yl)benzamide;
4-chloro-N-(3-cyclopropyl-1H-pyrazol-5-yl)benzamide;
N-(3-cyclopropyl-1H-pyrazol-5-yl)-1-benzothiophene-2-carboxamide;
N-(3-cyclopropyl-1H-pyrazol-5-yl)[1,1'-biphenyl]-4-carboxamide;
N-(3-cyclopropyl-1H-pyrazol-5-yl)-3-phenylpropanamide;
Methyl 4-{[(3-cyclopropyl-1H-pyrazol-5-yl)amino] carbonyl}benzoate;
4-([(3-cyclopropyl-1H-pyrazol-5-yl)amino] carbonyl}benzoic acid;
N-(3-cyclopropyl-1H-pyrazol-5-yl)-3-bromobenzamide;
N-(3-cyclopropyl-1H-pyrazol-5-yl)-3,4-dichlorobenzamide;
N-(3-cyclopropyl-1H-pyrazol-5-yl)-2-bromobenzamide;
N-(3 -cyclopropyl-1H-pyrazol-5-yl)-3-methoxybenzamide;
N-(3-cyclopropyl-1H-pyrazol-5-yl)-3-trifluoromethylbenzamide;
N-(3-cyclopropyl-1H-pyrazol-5-yl)-4-methoxybenzamide;
4-butoxy-N-(3-cyclopropyl-1H-pyrazol-5-yl)benzamide;
N-(3-cyclopropyl-1H-pyrazol-5-yl)-1H-indole-2-carboxamide;
N-(3-cyclopropyl-1H-pyrazol-5-yl)-2-[5-(2,6-difluorobenzyl)-2-methoxyphenyl]acetamide;
and
N$^1$-(3-cyclopropyl-1H-pyrazol-5-yl)terephthalamide;
or a pharmaceutically acceptable salt thereof.

17. A process for preparing the 3-amino-pyrazole derivative of claim 11, or the pharmaceutically acceptable salt thereof, comprising:

(a) reacting a compound represented by formula (II):

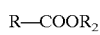  (II)

wherein
R is as defined in claim 11, and
$R_2$ is an alkyl group,
with acetonitrile in the presence of a basic agent, to produce a compound represented by formula (III):

  (III)

wherein R is as defined above;

(b) reacting a compound represented by formula (III) with hydrazine hydrate, to produce a compound represented by formula (IV):

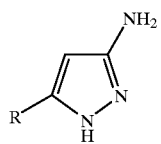  (IV)

wherein R is as defined above;

(c) oxidizing the compound represented by formula (IV), to produce a compound represented by formula (V):

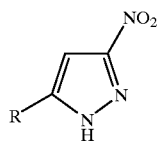  (V)

wherein R is as defined above;

(d) reacting the compound represented by formula (V) with tert-butoxycarbonyl anhydride, to produce a compound represented by formula (VI):

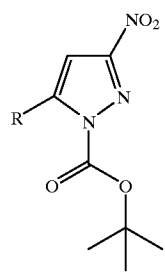  (VI)

wherein R is defined above;

(e) reducing the compound of formula (VI), to produce a compound represented by formula (VII):

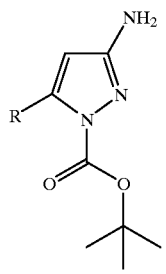  (VII)

wherein R is as defined above;

(f) reacting the compound represented by formula (VII) with a compound represented by formula (VIII):

  (VIII)

wherein
X is hydroxy, and $R_1$ is as defined in claim 11, to produce a compound represented by formula (IX):

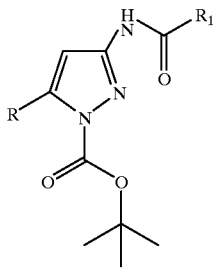

(IX)

wherein R and $R_1$ are as defined above; and (g) hydrolyzing the compound represented by formula (IX) in an acidic medium, to produce a compound represented by formula (I), wherein R and $R_1$ are as defined above.

18. The process of claim 17, further comprising converting the 3-amino-pyrazole derivative represented by formula (I) into another derivative represented by formula (I), and/or into a salt thereof.

19. A compound represented by formula (V):

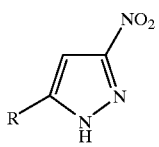

(V)

wherein R is a $C_3$–$C_6$ cycloalkyl group optionally substituted with a straight or branched $C_1$–$C_6$ alkyl group.

20. A process for preparing the 3-amino-pyrazole derivative of claim 11, or the pharmaceutically acceptable salt thereof, comprising:

(a) reacting a compound represented by formula (IV):

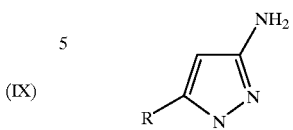

(IV)

with a compound represented by formula (VII):

$R_1$—COX  (VIII)

wherein
R and $R_1$ are as defined in claim 11, and
X is hydroxy or a suitable leaving group,
to produce a compound represented by formula (X):

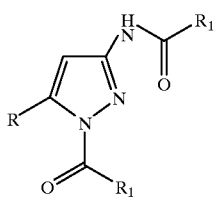

(X)

wherein R and $R_1$ are as defined above; and (b) selectively hydrolyzing the compound represented by formula (X) in a basic medium, to produce a (5)-amino-pyrazole derivative represented by formula (I).

21. A pharmaceutical composition, comprising the (5)-amino-pyrazole derivative of claim 11 and at least one pharmaceutically acceptable carrier and/or diluent.

22. The method of claim 11, wherein R is a $C_3$–$C_4$ cycloalkyl group optionally substituted by a straight or branched $C_1$–$C_6$ alkyl group.

23. The method of claim 22, wherein R is unsubstituted.

24. The method of claim 11, wherein R is a cyclopropyl group optionally substituted by a straight or branched $C_1$–$C_6$ alkyl group.

25. The method of claim 24, wherein R is unsubstituted.

* * * * *